United States Patent
Kroll et al.

(10) Patent No.: US 8,540,641 B2
(45) Date of Patent: Sep. 24, 2013

(54) PERSONALIZED ACTIVITY MONITOR AND WEIGHT MANAGEMENT SYSTEM

(75) Inventors: Ryan Kroll, Orono, MN (US); Elise P. Brock, Minneapolis, MN (US); James A. Meyer, Shoreview, MN (US); Marc A. Seaberg, Bloomington, MN (US); Thomas G. Hudson, Excelsior, MN (US); E. Andrew Wood, Rochester, MN (US); Gary A. Stein, Oakdale, MN (US); James A. Levine, Orono, MN (US)

(73) Assignee: Gruve Technologies, Inc., Andover, MN (US)

( * ) Notice: Subject to any disclaimer, the term of this patent is extended or adjusted under 35 U.S.C. 154(b) by 0 days.

(21) Appl. No.: 13/491,306

(22) Filed: Jun. 7, 2012

(65) Prior Publication Data
US 2013/0006125 A1 Jan. 3, 2013

Related U.S. Application Data

(63) Continuation of application No. 12/552,167, filed on Sep. 1, 2009, now abandoned.

(60) Provisional application No. 61/100,586, filed on Sep. 26, 2008.

(51) Int. Cl.
*A61B 5/08* (2006.01)
*A61B 5/00* (2006.01)

(52) U.S. Cl.
USPC .......................................... 600/485; 600/300

(58) Field of Classification Search
USPC .......................................... 600/300, 485, 531
See application file for complete search history.

(56) References Cited

U.S. PATENT DOCUMENTS

| | | | |
|---|---|---|---|
| 5,788,655 | A | 8/1998 | Yoshimura et al. |
| 6,701,271 | B2 | 3/2004 | Willner et al. |
| 6,810,349 | B2 | 10/2004 | Westerterp et al. |
| 7,075,537 | B2 | 7/2006 | Simond et al. |
| 7,789,800 | B1 | 9/2010 | Watterson et al. |
| 2001/0049470 | A1* | 12/2001 | Mault et al. ................ 600/300 |
| 2002/0170193 | A1 | 11/2002 | Townsend et al. |
| 2003/0074151 | A1 | 4/2003 | Rapp |
| 2005/0181386 | A1 | 8/2005 | Diamond et al. |

FOREIGN PATENT DOCUMENTS

| | | |
|---|---|---|
| WO | 01/52718 A2 | 7/2001 |
| WO | 2006/121758 | 11/2006 |
| WO | 2007/143095 | 12/2007 |

OTHER PUBLICATIONS

Snodgrass et al. "The Influence of Basal Metabolic Rate on Blood Pressure Among Indigenous Siberians". American Journal of Physical Anthropology 000:000-000 (2008).*

* cited by examiner

*Primary Examiner* — Patricia Mallari
*Assistant Examiner* — Christian Jang
(74) *Attorney, Agent, or Firm* — Vidas, Arrett & Steinkraus

(57) ABSTRACT

A weight management system comprised of a body worn device which interfaces periodically with a computer. The established weight goals of the user are translated by the computer into daily activity targets and downloaded into the device. The device monitors the user's activity, offering progress status toward the daily activity target. Further, the device alerts the user of excessive sedentary periods which depress metabolic indicators. The activity targets, allowed length of sedentary periods and suggested activities to reach goal are specific to the individual based on their biometrics and living environment. The computer provides historical tracking of activity for motivational and coaching purposes.

1 Claim, 17 Drawing Sheets

Device Configuration Page

Based on your inputs, your device settings are as follows:

ECP: 54 minutes
ECP Alerts: 10 minutes prior to entering ECP, total of 3 alerts
Sleep Hours (turn off ECP alerts): 10 PM – 6AM RMR: 1600 calories per day Objective: lose weight Calorie Goal: 2500/day (900 through activity)

Red 0 - 225
Orange = 225 – 450
Yellow = 450 - 675
Blue= 675–899
Green = 900+

FIG. 3

PERSONALIZED ACTIVITY MONITOR AND WEIGHT MANAGEMENT SYSTEM

CROSS-REFERENCE TO RELATED APPLICATIONS

This application is a continuation application of U.S. application Ser. No. 12/552,167, filed on Sep. 1, 2009, which claims the benefit of U.S. Provisional Patent Application Ser. No. 61/100,586 filed on Sep. 26, 2008, the entire disclosures of which are hereby incorporated herein by reference.

STATEMENT REGARDING FEDERALLY SPONSORED RESEARCH

This invention was made with government support under DK066270 awarded by the National Institutes of Health. The government has certain rights in the invention.

BACKGROUND OF THE INVENTION

1. Field of the Invention

Embodiments of the present invention relate to a weight management system including a web application service and a body worn activity monitoring device.

2. Description of the Related Art

Obesity in humans in the United States, as well as in other parts of the world, is reaching epidemic proportions. Desk-bound occupations, long commutes, cheap and convenient fast food, over-sized food portions, increased television watching, and decreased exercise have all contributed to bulging waistlines.

It is difficult to open a magazine or turn on the television without seeing an advertisement for pills, creams, or home exercise equipment, all promising to help the desperate consumer lose weight. In spite of the billions of dollars spent annually on these products, obesity rates continue to rise.

What these products ignore is the simple fact that if the amount of calories ingested is greater than the amount of calories burned, there will be a weight gain over time. Similarly, if the amount of calories burned is greater than the amount of calories ingested, there will be a weight loss over time. Measuring and displaying the amount of calories burned through physical activity provides useful information to the user.

Devices for measuring activity have been around for years. The pedometer, a device for counting the number of steps taken, has been around for hundreds of years but can be notoriously inaccurate. A number of devices on the market today attempt to count the amount of calories burned throughout the day, but are based upon the classical work-energy theorem or gross estimations with body weight. At least one of the goals of the present invention is to provide personalized accuracy and relevance, based on the user's individual biometrics and living environment.

In addition to the devices on the market, devices and methods for measuring and displaying physical activity are described in U.S. Pat. Nos. 5,788,655, 6,810,349, and 7,075,537, as well as PCT publications WO 2006/121758 and WO 2007/143095, the entire contents of each being expressly incorporated by reference herein.

A critical component in burning calories, and thus weight loss, is maintaining an elevated metabolic rate. Jogging 30 minutes several times each week, for example, is helpful in burning calories by elevating the metabolic rate for that period of time. However, performing a number of smaller motions throughout the course of the day maintains an elevated metabolic rate and burns as many or more calories than a half-hour of jogging. Yet for a variety of reasons many people may go for several consecutive hours at work, for example, without so much as standing up from their desk. Prolonged sedentary behavior dramatically reduces a person's metabolic rate, thereby slowing the rate at which calories are burned.

At least one of the goals of the present invention is to provide a device that monitors inactivity and proactively alerts the user of prolonged sedentary behavior to prevent a drop in their metabolic rate.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below. A brief abstract of the technical disclosure in the specification is provided for the purposes of complying with 37 C.F.R. §1.72.

BRIEF SUMMARY OF THE INVENTION

In at least one embodiment, the invention is directed to a device for alerting a user of prolonged sedentary behavior. The device comprises a controller, one or more tri-axial accelerometers for monitoring physical activity, and a timer. The controller has one or more inputs and one or more outputs, and the controller calculates a predetermined time of inactivity from a first algorithm. Each of the one or more tri-axial accelerometers has one or more outputs in communication with the one or more controller inputs. The one or more tri-axial accelerometers produce first accelerometer signals and second accelerometer signals. The first accelerometer signals correspond to the user being inactive and the second accelerometer signals correspond to the user being active. The timer has one or more inputs and one or more outputs, with at least one input of the timer being in communication with at least one output of the controller. A controller output outputs a first controller signal to the timer upon detection of a first accelerometer signal, thereby starting the timer. An output of the timer outputs a first timer signal if the timer reaches the predetermined time of inactivity. The controller outputs a user alert signal upon receiving the first timer signal.

In some embodiments, the invention is directed towards a method for alerting a user of prolonged sedentary behavior. The method comprises providing a controller, the controller having at least one input and at least one output. The method further comprises providing a timer, the timer having at least one input and at least one output, an input of the timer is in communication with the an output of the controller. The method further comprises calculating a predetermined time according to a first algorithm. The method further comprises monitoring physical activity using one or more tri-axial accelerometers. The accelerometer(s) has one or more outputs in communication with the one or more inputs of the controller. The accelerometer(s) produce first accelerometer signals and second accelerometer signals. First accelerometer signals correspond to the user being inactive and second accelerometer signals correspond to the user being active. The method further comprises outputting a first controller signal to the timer upon detection of a first accelerometer signal. The method further comprises outputting a second controller signal to the timer upon detection of a second accelerometer signal. The method further comprises starting the timer upon the timer receiving the first controller signal. The method further comprises pausing the timer upon the timer receiving the second controller signal. The method further comprises resetting the timer upon the timer receiving a reset signal from the controller. The method further comprises alerting the user if the timer reaches the predetermined time.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIG. 3 is a diagram of a device configuration screen, in accordance with at least one embodiment of the present invention.

DETAILED DESCRIPTION OF THE INVENTION

Figure 1:
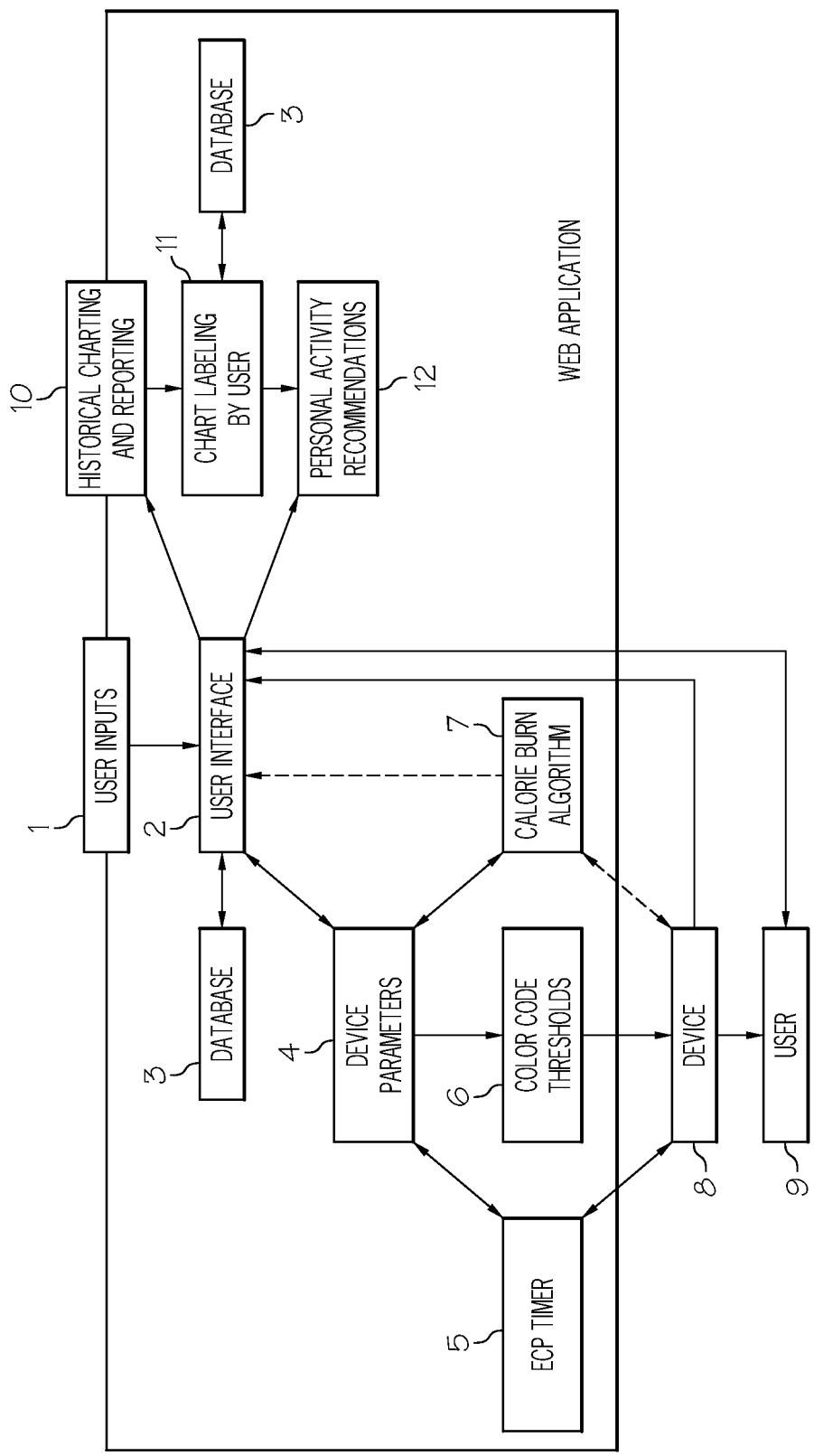
FIG. 1 is a diagram of a weight management system incorporating the use of activity sensing devices and online web resources, in accordance with at least one embodiment of the present invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Some embodiments of the present invention are directed towards a weight management system comprised of a web application service and a body worn activity monitoring device. Using information input by the user, the web application creates a personalized daily goal for amount of physical activity and calories burned, dependent on a users desire to maintain or lose weight and their individual biometrics. The web-application also determines the user's Energy Conservation Point™, the point at which a user's metabolism begins to slow as a result of too much prolonged sedentary behavior. In addition to these parameters, the web-application creates a daily activity plan, which will help users reach activity and calorie burning goals. It also provides a platform for social networking where users of the system can interact with one another and participate in a rewards and incentive system via the internet.

When synchronized with the web-application, the daily activity target and ECP values are configured into the device, allowing for real time tracking of goals. The device performs a number of operations: monitoring and recording the user's daily physical activity using an acceleration sensor, communicating compliance with the pre-established activity plan created by the web-application and offering motivational feedback to the user by means of audible, tactile, and visual feedback mechanisms. The device warns the user with audible and/or tactile alerts when the ECP point is near. The device periodically communicates with the web-application, uploading the activity data for historical tracking via charts and graphs, and more in-depth analysis. This in-depth analysis, coupled with changes in the individuals body statistics (weight, BMI, other) dynamically updates the algorithm parameters, daily targets and ECP interval.

The system allows unprecedented accuracy in personal calibration of the activity monitoring device to the individual. Many health clubs and fitness trainers today provide $VO_2/VCO_2$ calorimetry services, where an individual's calorie burn at rest, or resting metabolic rate (RMR), and various activity levels can be precisely measured. When the activity monitoring device is worn during the $VO_2$ tests, the outputs of the calorimeter and the activity monitoring device can be correlated by the system. This allows future user motion recording by the activity monitoring device to be accurately translated into calorie expenditure. When calorimetry data is not available, a user is matched by a number of other biometric data including, but not limited to weight, height, age, and gender into a population database of calorimeter profiles.

The system delivers personalized suggestions for activity based on current deficit calories relative to the daily plan, historical knowledge of individual calorie expenditure across a range of activity types and knowledge of a user's environment and its opportunities for certain activities such as walking or stair climbing.

At least some embodiments of the present invention are directed towards a weight management and wellness system comprised of a body worn device that works in conjunction with a computer application. The body worn device monitors body movements and activity patterns, provides real time feedback to the user about activity habits and daily calorie burn progress, and synchronizes with the computer application to receive user settings, provide historical reporting and user interface. The computer application gathers information about the user in order to calibrate the device to the individual for accurate calorie burn measurements, assigns personalized activity plans and targets to the user, and sets device parameters including an Energy Conservation Point alert and real time progress status. The computer application also performs the following functions: provides historical activity progress reporting and trending using a color coding system; provides historical reporting and trending of weight and other health measures; provides calorie intake guidelines and tracking capabilities; provides activity recommendations, based on a user's past historical calorie burn; provides social networking; and provides rewards and incentives.

Unique features of the system include its personalized calibration capability. The web-application, device and outputs are uniquely calibrated to each user based on inputs to the system. Personally calibrated items include:

Energy Conservation Point—A user is notified when he or she has been sedentary for too long. This notification is done by a vibration emitted by the device. The web application also tracks ECP occurrences and trends.

Color Code Progress reporting—as a user burns calories throughout the day—they will move through different color zones. The thresholds for these color zones are unique to each individual, based on their unique metabolic rates and calorie burn goal. When a user reaches their goal, they are in the Green Zone.

Personalized Activity recommendations based on:
Health and Environmental Awareness—At program initiation, the user will answer a series of questions regarding their health, diet, and environment. The responses to these questions will determine what recommendations the system generates for each user.

Historical awareness—When a user labels their charts, the system stores how many calories an individual burns doing certain activities. The system then generates activity recommendations based on this information that are custom to the number of calories a person has remaining to burn to reach their goal.

The web interface or computer application may be resident on a personal computer, PDA, cell phone (such as Apple's iPhone), MP3 player (such as Apple's iPod®) or a public kiosk computer. In at least one embodiment, the application is a web service accessible via the Internet. In some embodiments, the computer application allows the software to be run on a device that never accesses the web.

In at least one embodiment, the cell phone, MP3 player, PDA, or other stand-alone device can include appropriate acceleration sensors, sedentary alert mechanisms, and host the algorithms and methods specified herein.

Referring now to the drawings, a block diagram of a weight management system incorporating the use of activity sensing devices and online web resources is shown in FIG. 1. A user provides personal information (1) via a web based user interface (2). This information is stored in a database (3) and used in setting device parameters (4). These parameters include an individual's Energy Conservation Point timer (5) and color code threshold values (6), and are sent to the body worn device (8) via a USB download. Parameters for the calorie burn algorithm (7) are determined and provided for use in the device or web application. In some embodiments, calories are calculated external to the device in the web application. The device (8) then displays the color code (6) and ECP alerts (5) to the user (9). Additionally, the device (8) synchronizes via USB with the web-application to provide the user's (9) activity information, as measured by the device (8). After synchronization, the user interface (2) displays to the user (9) historical charts and reports (10) which can be labeled (11) by the user (9). Such labels, along with associated calories burned as reported in the historical charts (10) are stored in a database (3), and later queried in order to provide activity recommendations (12) that are personalized to the user (9) based on his or her past calorie burn information.

Figure 2:
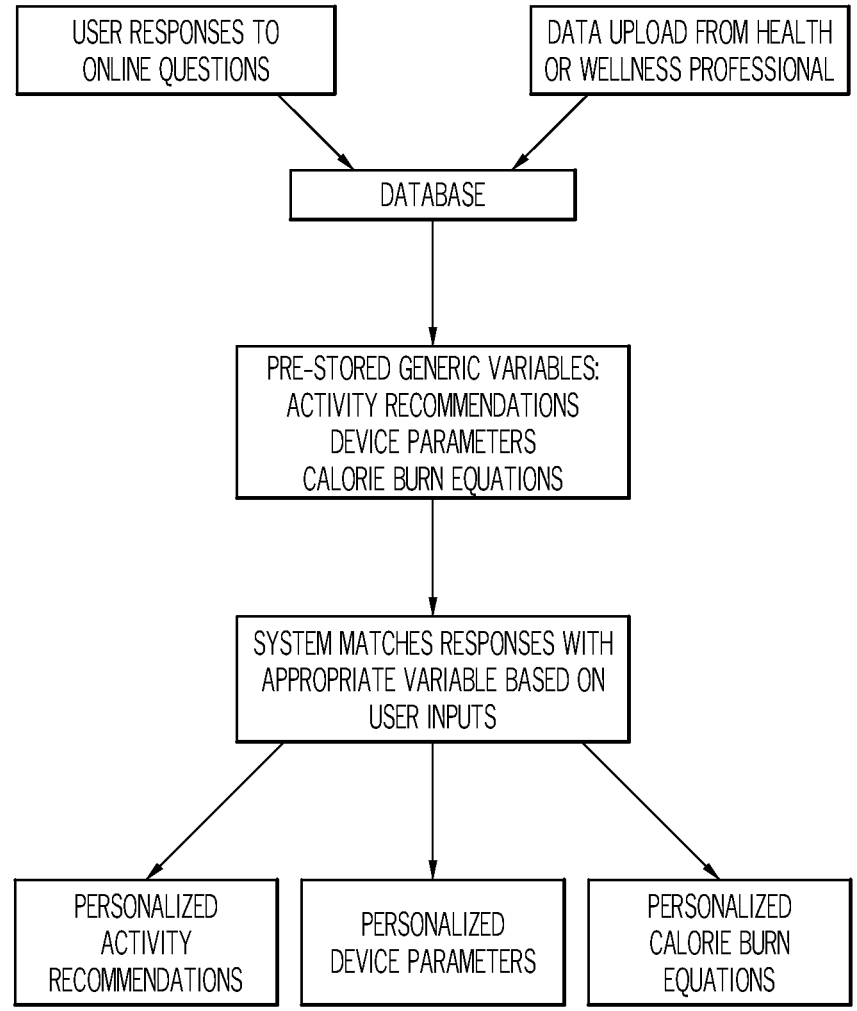
FIG. 2 is a diagram depicting the inputs and steps of matching an individual with personalized activity recommendations and device calibration, in accordance with at least one embodiment of the present invention.

Referring now to FIG. 2, a block diagram depicts the inputs and steps of matching an individual with personalized activity recommendations and device calibration through a web application. At the start of the program and at certain intervals throughout the program, the user provides personal information via the web application. These inputs are generated by online questionnaires and/or biometric tests. The web application asks the user a series of questions related to their environment, health and biometrics, lifestyle, diet, activity levels, and other relevant factors. Online lifestyle questions include, but are not limited to, the following:

Goal: weight loss or maintenance

Weight, height, age, gender, waist size, hip measurement

Daily sleep habits, hours and duration

Physical and health conditions or limitations

Work environment: seated work, on your feet, physical activity, stairs, elevators, indoors vs. outdoors, commute duration Enjoyable physical activities: walking, hiking, running, biking, swimming, aerobics, gardening, yard work, tennis Average daily diet: In one embodiment, the user can select one of several sample diets that they feel is representative of their own personal diet. These sample diets are associated with a predetermined calorie intake level. In another embodiment, users can utilize a detailed calorie tracking program where they are able to select foods that they eat from a database of foods which correlate with a known calorie amount. In yet another embodiment, users are able to simply enter a numerical value for their calorie intake based on what they've learned from external tracking methods. In yet another embodiment the application asks the user a series of questions about their diet which will lead to an estimated calorie intake level.

In some embodiments, users are also able to input information obtained from a health or wellness professional, such as lipid profiles or measured metabolic rates. Accepted inputs from a health or wellness professional include, but are not limited to the following:

Plasma lipid and glucose profiles

Resting heart and respiration rates

Calorimeter measures: resting metabolic rate (RMR), metabolic rates at various walking speeds.

User inputs are stored in a system database, and are used to determine device parameters, calorie burn equations, and activity recommendations that are most closely aligned with the users responses. These inputs are used to uniquely calibrate the device to an individual and are downloaded to the device. FIG. 3 depicts a device configuration page that is created by the web application, based on these inputs.

An individual's daily calorie expenditure can be divided into a resting metabolic rate (RMR) component and an activity based component:

Total daily calories=calories$_{RMR}$+calories$_{activity}$.

RMR can be directly measured by a health or wellness professional and the result entered into the system.

When RMR from calorimetry is not available, RMR is calculated from the following equation:

$$RMR = K_1 * W * (1 - K_2 * W/H^2) + K_3 * H - K_4 * A - K_5 * G + K_6 * D - K_7 * S + K_8 \text{ where}$$

RMR is kilocalories/day

W is weight in kg

H is height in cm

A is age in years

G is gender, where male=1 and female=0

D is diastolic blood pressure in mmHg

S is systolic blood pressure in mmHg $K_1$ is in the range of about 8 to about 14

$K_2$ is normally in the range of about 80 to about 120, but can also assume a value of zero $K_3$ is in the range of about 4 to about 8

$K_4$ is in the range of about 3 to about 7

$K_5$ is in the range of about 150 to about 180

$K_6$ is in the range of 0 to about 7

$K_7$ is in the range of 0 to about 5

$K_8$ is in the range of 0 to about 20

The activity based calorie component is determined from device captured and recorded physical movements. In some embodiments, the expended calories are calculated within the device. In at least one embodiment, the device reports motion in terms of activity units (AU) and calories are calculated external to the device by the web application after the upload of the activity data during synchronization.

When calorimetry data of physical activity, such as treadmill walking, is available, an accurate correlation of the device AUs and measured calories is established for an individual through the following procedure:

1. A subject wears the device while treadmill walking at 1, 2 and 3 miles per hour (mph).
2. An indirect calorimeter measures the actual calorie consumption of the subject during the walking tests.
3. The resting metabolic rate (RMR) is also captured by the calorimeter.
4. A log-linear regression correlation between the device AUs and actual calories across the 3 walking data points is performed, establishing a predictive activity based calorie expenditure equation for the subject:

$$\ln(\text{kcal}_{activity}/0.5 \text{ minute}) = m * \ln(AU) + b$$

where m and b are constants as determined by a least squares regression, with ln(AU) and ln(kcal$_{activity}$) being the independent and dependent variables respectively.

Figure 4:
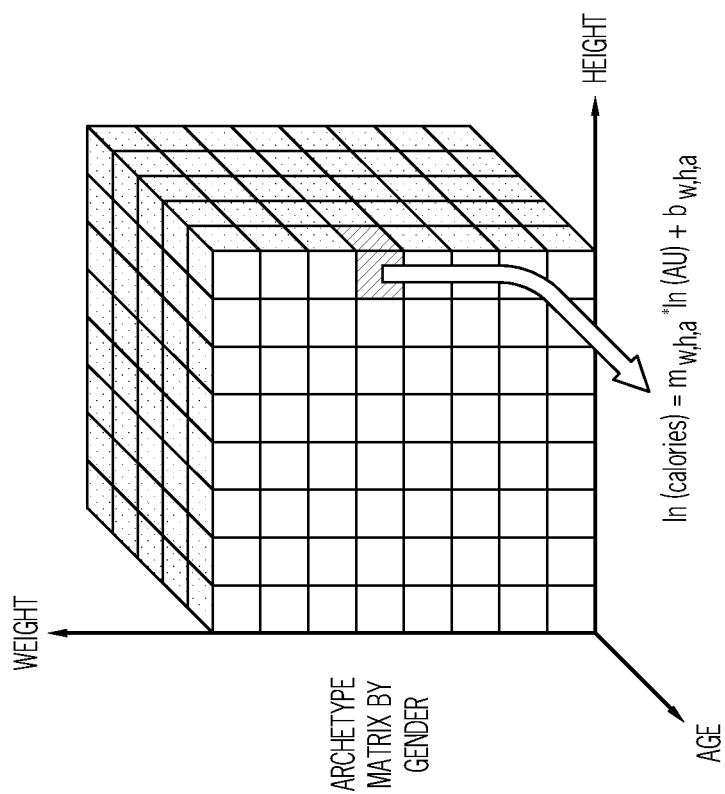
FIG. 4 depicts the inputs of the archetype determination, which results in the predictive calorie expenditure equation to be used for the individual, in accordance with at least one embodiment of the present invention.

When calorimetry data is not available, the user's height, weight, age, and gender are mapped to a pre-established archetype. Each archetype has a predetermined predictive calorie expenditure equation, as seen in FIG. 4. The constants $m_{w,h,a}$ and $b_{w,h,a}$ of each archetype are averages of the calorimetry derived predictive equations across a subject population. The subject population is seeded with an initial characterization group (200-500 subjects) and expands as additional participants with calorimetry join the program. The constants $m_{w,h,a}$ and $b_{w,h,a}$ ranges are 0.05 to 1.3 and −9 to 0.5 respectively. From these constants, an activity based calorie expenditure equation can be determined. In some embodiments, an alternate activity unit to calorie calculation is used. Activity units are used to classify to a user's speed or activity, which then indexes an activity multiplier.

Total kcal=RMR*ActivityMultiplier

RMR is determined per individual by the calorimeter or equation methods previously described. Activity units classify speed or activity based on thresholds as shown in the table below

| Activity Units Threshold | Speed | Activity Multiplier |
|---|---|---|
| | Sedentary | 1.0 |
| $T_1$ | | |
| | Standing | 1.1 |
| $T_2$ | | |
| | 1 mph | 2.0 |
| $T_3$ | | |
| | 2 mph | 2.5 |
| $T_4$ | | |
| | 3 mph | 3.3 |
| $T_5$ | | |
| | 4 mph | 5.0 |
| $T_6$ | | |
| | High | 8.0 |

Where:

$T_1$ is in the range of about 240-about 360, $T_2$ is in the range of about 880-about 1320, $T_3$ is in the range of about 2000-about 3000, $T_4$ is in the range of about 3360-about 5040, $T_5$ is in the range of about 5120-about 7680, and $T_6$ is in the range of about 8800-about 13200.

Speed could also be calculated from distance over time as determined by coordinates from an integral global positioning system (GPS).

Referring now to a user's activity, as an individual continues to burn calories throughout the day, some embodiments of the device display can transition between multiple colors. For example, the display can begin with Red when there has been little to no activity, and end with Green when the user has achieved their daily calorie burn goal. Some embodiments have five color zones, thereby allowing the user to be visually notified of their progress from red to green throughout the day. The device displays the user's current color zone in real-time throughout the day.

With respect to the web application, the graphs or charts also display the color achieved for the day. Historical charts depict the color zone that the user was in at each hour of the day. In at least one embodiment of the device that uses five color zones, the color zones are calculated using the following formulas, where "Goal"=the user's total daily calorie burn goal, and RMR is the user's "Resting Metabolic Rate":

Red=0 to 0.25(Goal-RMR)

Orange=0.25(Goal-RMR) to 0.5(Goal-RMR)

Yellow=0.5(Goal-RMR) to 0.75(Goal-RMR)

Blue=0.75(Goal-RMR) to Goal-1

Green=Goal+

Because the daily goal and the RMR are unique to the user, the resulting color zone thresholds are personalized to each individual. A person of ordinary skill in the art will understand some embodiments of the invention can have more color zones, less color zones, or different colors, and that these colors can be displayed in different formats, media, and devices.

Turning now to the Energy Conservation Point (ECP)™, the ECP has been developed as a warning threshold to prevent the onset of the negative physiological effects in an individual. Periods of sedentary activity are monitored and if they exceed the ECP threshold, a warning is offered to the user to attain physical activity. Bouts of activity distributed throughout the day prevent the ECP point from being reached.

Each user has an individual ECP duration threshold, where $ECP_{time}$ is inversely proportional to waist and BMI measures:

$$ECP_{time}=K_1/(waist*BMI)^{K_2} \text{ where}$$

$ECP_{time}$ is expressed in minutes,
waist is expressed in inches,
BMI is the standard definition of weight divided by height squared,
$K_1$ is a constant within the range 875-4000
$K_2$ is a constant within the range 0.2-0.9.

As individuals continue to synch their device with the web application, for example through an online web service, they will be given the opportunity to label time periods on the charts with an activity that they were performing during that time period. The system remembers these activities and the corresponding number of calories that were burned performing such activity. As a result, when a user later synchronizes their device with the website, the website provides a list of personalized recommended activities based on their history that will enable the individual to reach their calorie burn goal for the day.

Figure 5:
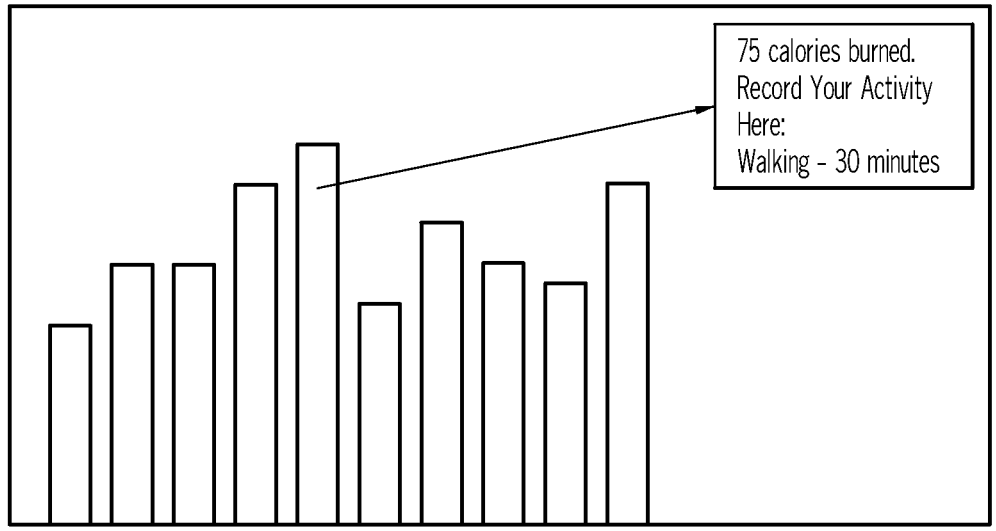
FIG. 5 depicts a web application calorie/activity daily charting and activity type marking, in accordance with at least one embodiment of the present invention.
Figure 6A:
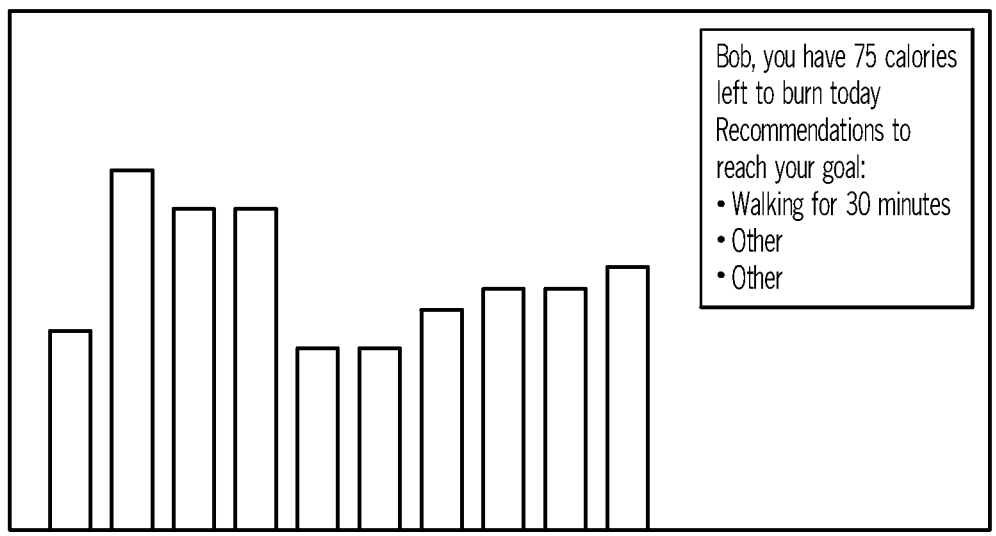
FIG. 6A depicts a web application calorie/activity daily charting with an activity recommendation based on historical learning, in accordance with at least one embodiment of the present invention.
Figure 6B:
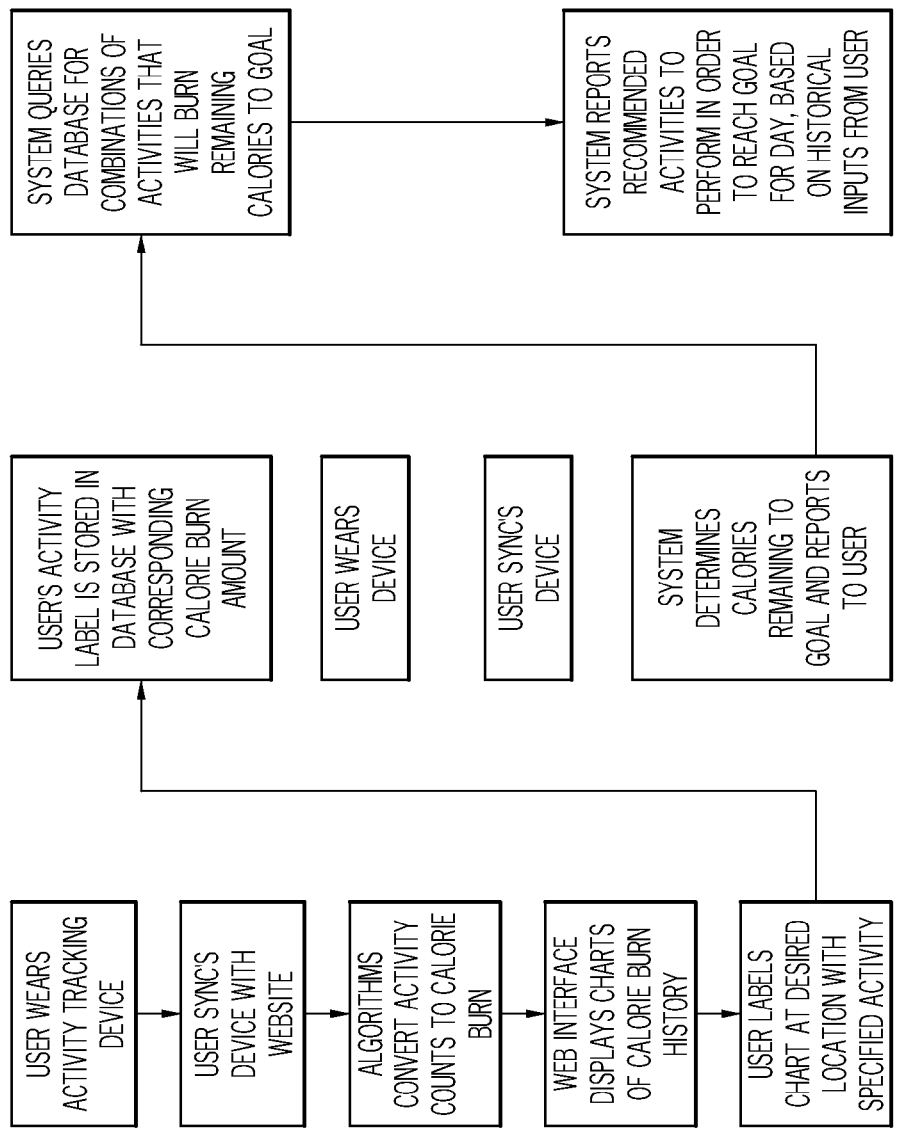
FIG. 6B is a flow diagram of activity recommendations based on historical association of calorie burn with activity types, in accordance with at least one embodiment of the present invention.

For example, if a user walks 30 minutes one day, synchs his device, and labels the charts accordingly, as in FIG. 5, the charts will not only display that 75 calories were burned during that walk, but it also remembers that when the user walks for 30 minutes, 75 calories are burned. So, if three days later the user is 75 calories short of achieving the daily goal, the system recognizes this when the device is synched. The system then recommends that the user take a 30 minute walk, as shown in FIG. 6A, in order to burn 75 calories in order to reach their daily goal. The system will also recommend other activities. These steps are summarized by the flowchart depicted in FIG. 6B.

Figure 7:
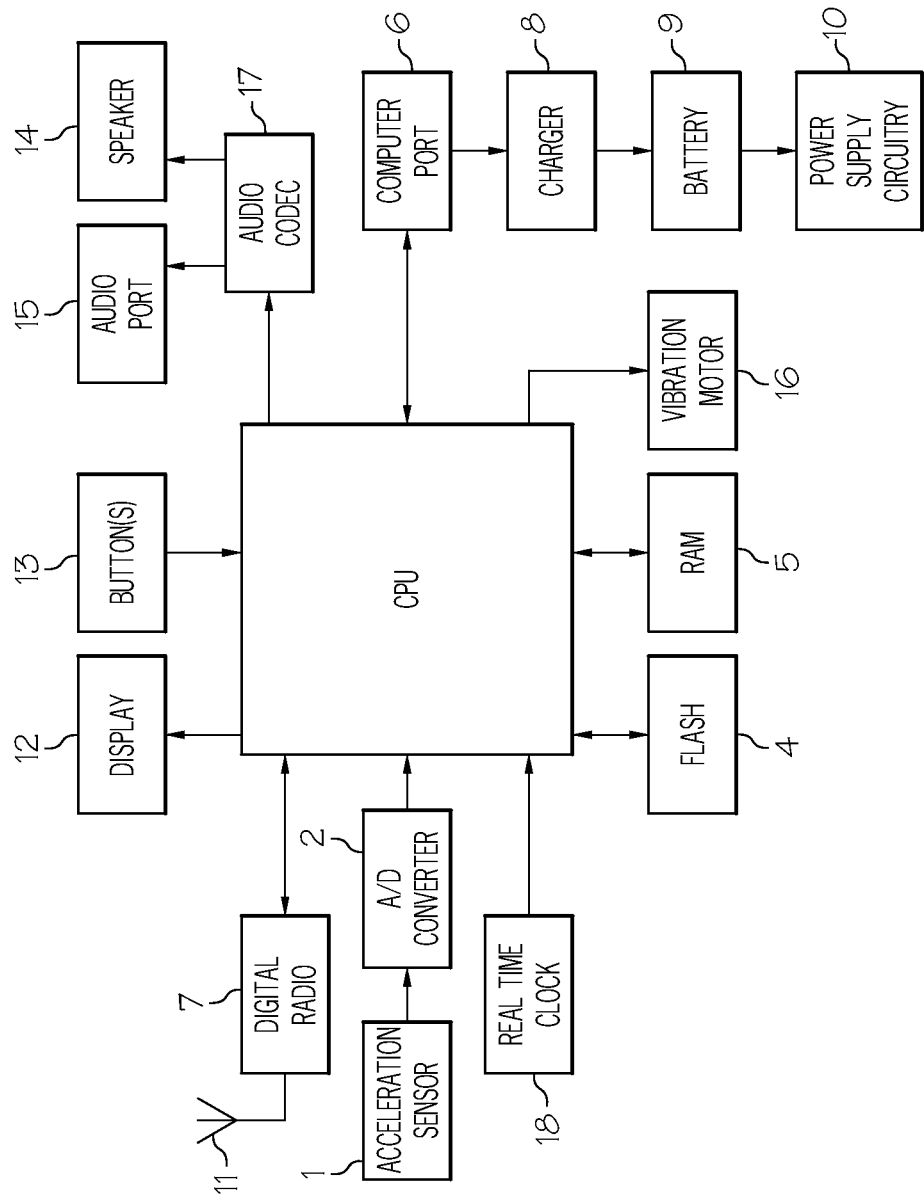
FIG. 7 is a block diagram of a body worn device for monitoring physical activity and reporting calorie burn information, in accordance with at least one embodiment of the present invention.

FIG. 7 depicts a block diagram of at least one embodiment of a body worn device for monitoring physical activity and reporting calorie burn information. The acceleration sensor (1) (or accelerometer) detects user body movements in two or more axes. Some embodiments of the present invention detect motion in the X, Y, and Z axes using a tri-axial accelerometer. The output of the sensor can be an analog voltage proportional to accelerations in the range from 0.005 to 6 G (where $G=9.8$ m/s$^2$). The analog voltage is converted to a digital representation by an analog to digital converter (2) which can be read by a CPU (3). The CPU executes a control program stored in memory (4). The memory can be non-volatile memory, for example FLASH or EEPROM, or other known memory. The control program processes the digital sensor readings, using temporary RAM (5), for example, for storage. The result are stored in memory (4) for later retrieval. Retrieval may be performed by a computer, cell phone, PDA or other device that interfaces via the computer port (6) or digital radio (7). The computer port may be USB, IEEE1394, RS232, or other serial interfaces. The computer port is also used for configuration, control program update and digital audio file download. The computer port may also supply external power to a charger circuit (8) to recharge the internal battery (9). As a body worn device, the internal battery provides all necessary electrical power when portable through the power supply circuitry (10).

Figure 15:
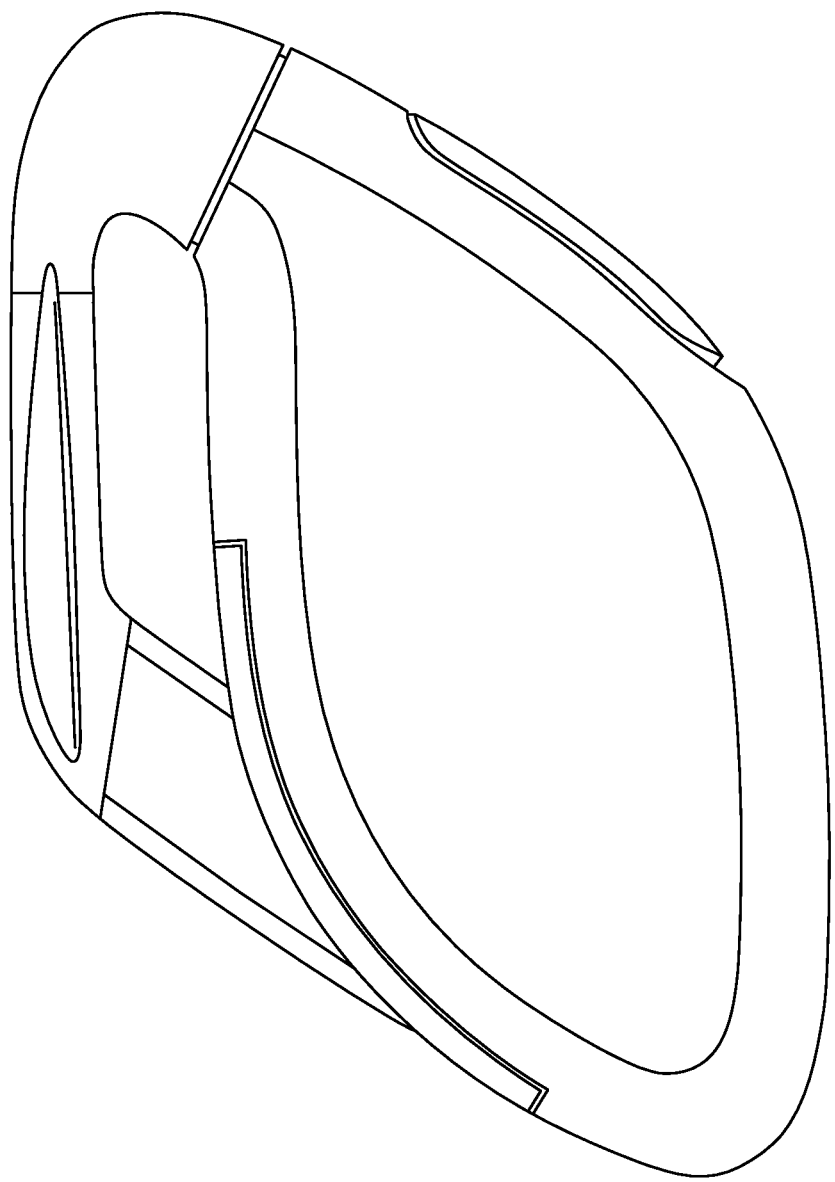
FIG. 15 is a front view of a body worn device, in accordance with at least one embodiment of the present invention.
Figure 16:
FIG. 16 is a perspective view of the body worn device in FIG. 15, in accordance with at least one embodiment of the present invention.
Figure 17:
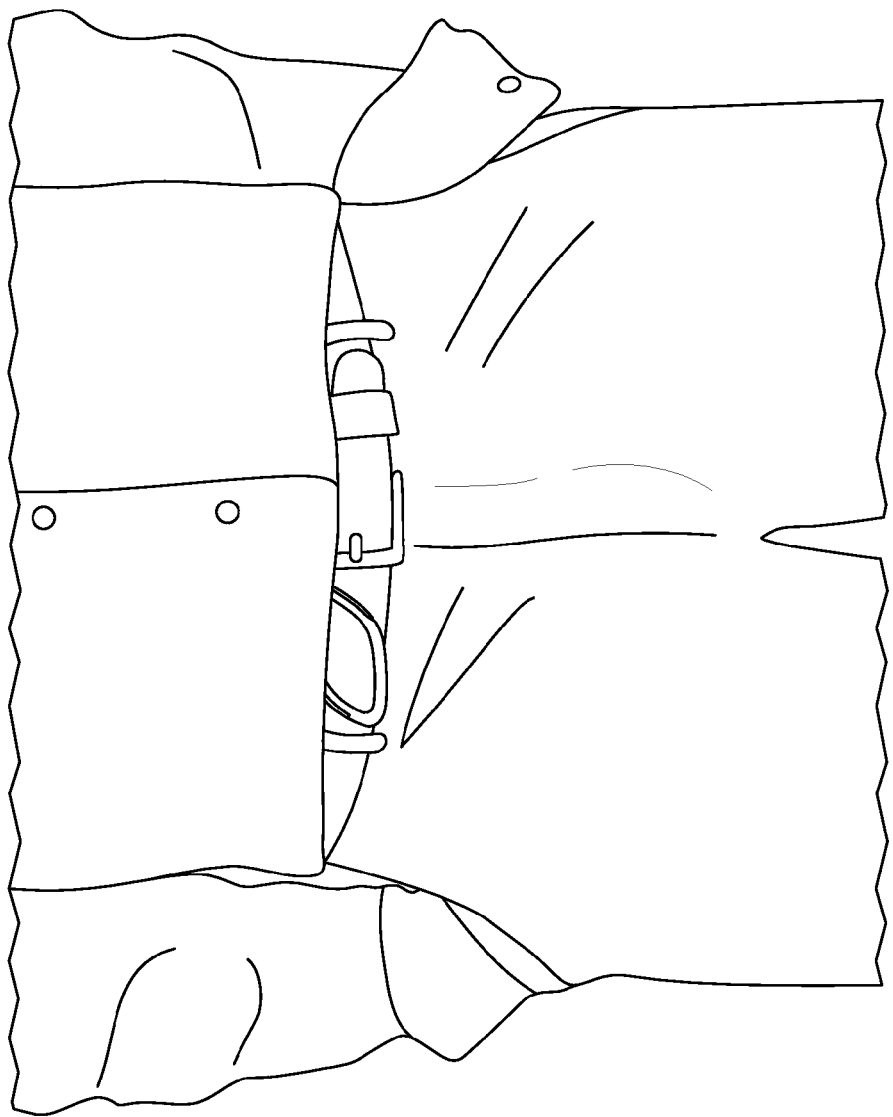
FIG. 17 is a front view of a person wearing the body worn device of FIG. 15, in accordance with at least one embodiment of the present invention.

FIGS. 15-17 depict various views of embodiments of the body worn device for monitoring physical activity and reporting calorie burn information.

The digital radio may be IEEE802.11 (WiFi), 802.15.1 (Bluetooth), 802.15.4 (Zigbee), 802.15.3 (UWB) or other wireless technologies including cellular and Wireless USB. The radio antenna (11) is internal to the device. The user interface is formed by a display (12), one or more buttons (13), an audio speaker (14) and port (15) and vibration motor (16). The device's display can present information such as total expended calories and activity intensities alphanumerically, graphically, or both. Progress toward a daily activity or calorie burn goal can be presented to the user on such a display or simple indicator lights. Multiple indicator lights can form a bar graph display, or progress can be indicated by different colors. User actuated buttons are inputs to the CPU and can initiate various functions including device on/off, display menu navigation, illumination of progress indicators, disabling alarms or time marking the acceleration sensor readings. The CPU can decode compressed digital audio stored in memory, which is converted to analog voltages by the codec (17) to drive an integral speaker (14) or audio port (15) for external earphones.

The audio may be user alerts such as low battery, sedentary time limit exceeded, spoken messages or tones signifying progress toward daily goals, spoken motivational messages, spoken educational health and wellness topics (book on tape) or recreational music. The vibrator motor (16) can be user enabled to silently alert the user for low battery or sedentary alarms. The alerts can also signal daily progress points with a different intensity or frequency of vibration. A real time clock circuit (18) allows the device to maintain time awareness so that alerts can be disabled during user defined sleep periods, which may vary from a weekday to weekend schedule. In some embodiments, several function blocks may be physically combined, such as the RAM (12) or Flash (13) being contained within the CPU (1) circuit.

The CPU processes user body movements in several ways. Individual axes of motion are used to determine body posture and infer activities, such as horizontal (sleeping or not worn) or vertical (awake and worn). Posture determination is achieved by the steady state or DC component of the acceleration sensor signal, signifying orientation with respect to gravity. Individual axes are also used for specific activities, such as a user step count. Steps are counted by monitoring the sensor signal vertical axis. A positive peak of sufficient duration and amplitude is classified and counted as a step. The resultant vector acceleration is calculated as the square root of the sum of squares of the individual axes. This composite acceleration (in G's) is proportional to the calorie expenditure of the user. Calories can be locally calculated on the device or externally by a retrieval device. When calculated locally, a display of calories per unit time and total calories from start of day can be displayed numerically or symbolically on the device. In a similar manner step counts can be displayed. When calories are calculated externally, the device indicates daily progress based on the percentages of accumulated composite acceleration. In addition to accumulated values, accelerations/calories and steps are stored in memory on a periodic basis to offer the user a review of the day(s) activities: which periods the user was active, which periods the user was sedentary and the activity intensity levels during those periods.

Figure 8:
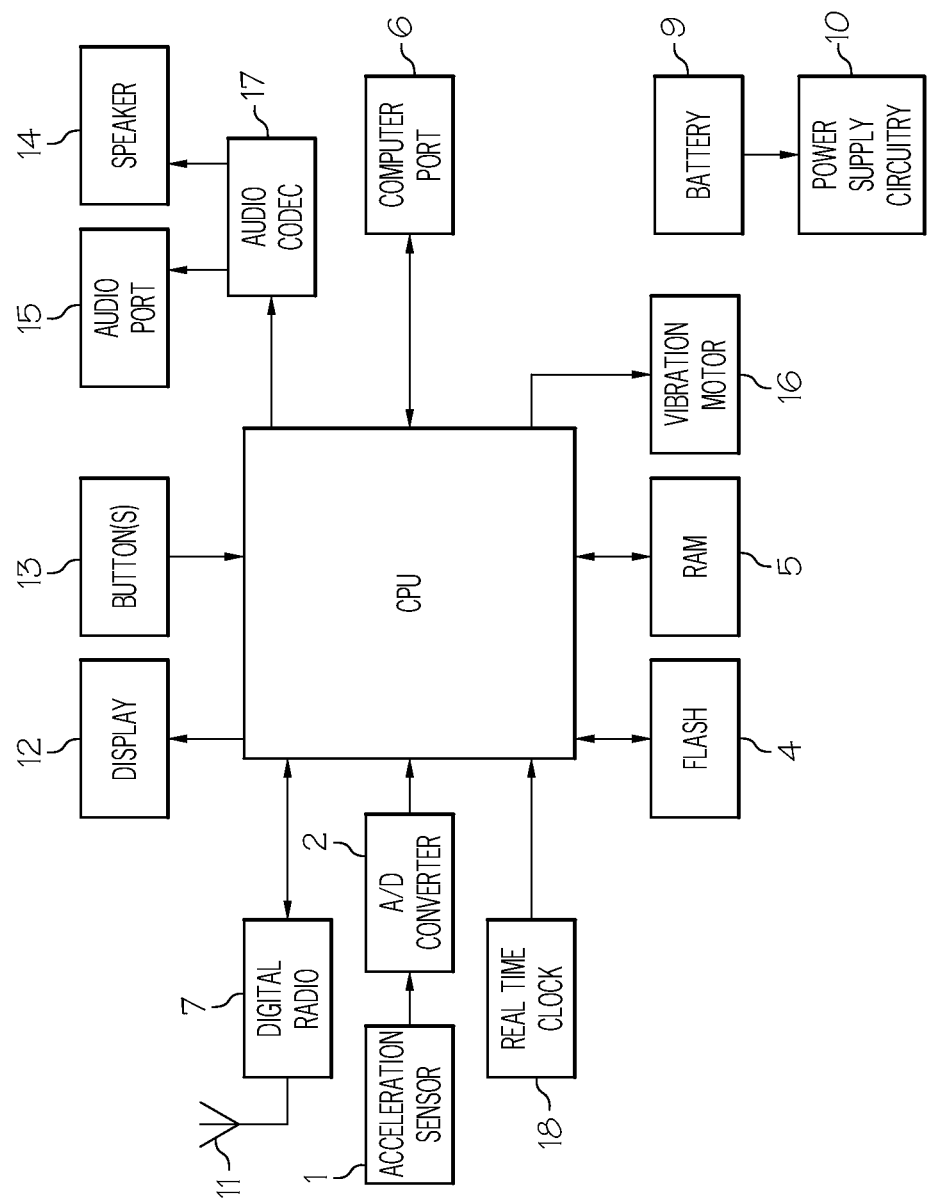
FIG. 8 is a block diagram of another body worn device for monitoring physical activity and reporting calorie burn information, in accordance with at least one embodiment of the present invention.
Figure 9:
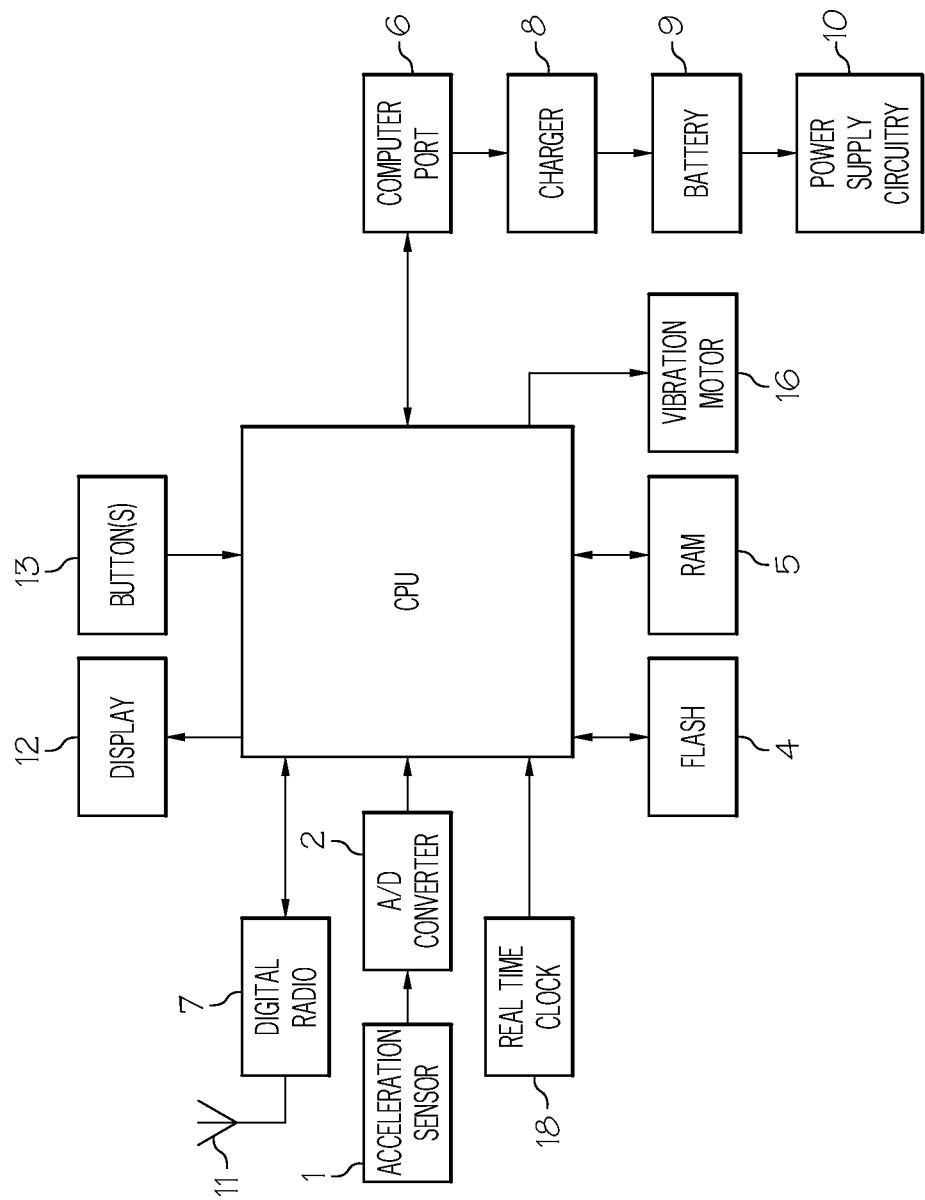
FIG. 9 is a block diagram of another body worn device for monitoring physical activity and reporting calorie burn information, in accordance with at least one embodiment of the present invention.

FIG. 8 illustrates an alternative embodiment of the body worn device of FIG. 7. In FIG. 8, the device includes a non-rechargeable, user replaceable battery (9); the charger circuit of FIG. 7 is no longer present. FIG. 9 illustrates a device with the audio capability removed. Several variations of devices can thus be envisioned.

Figure 10:
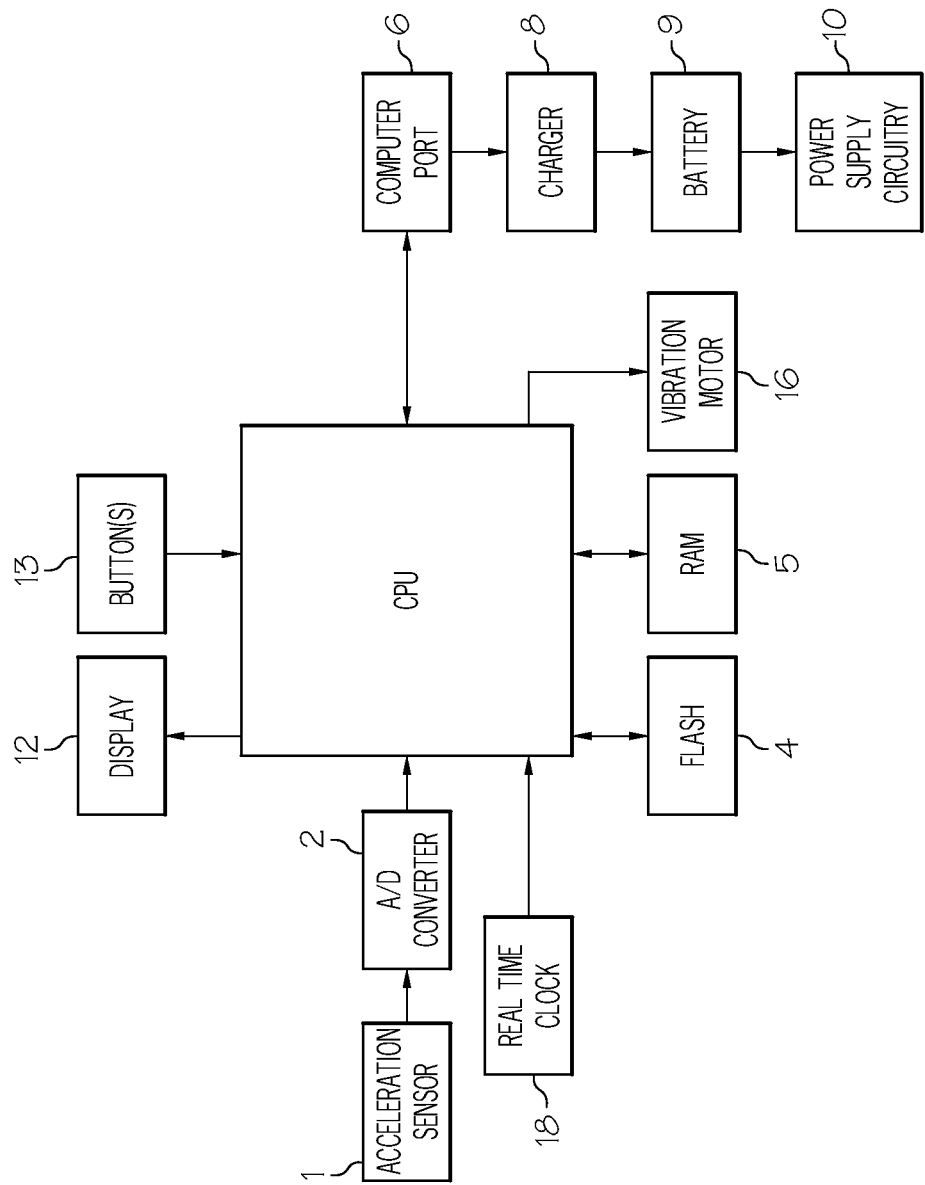
FIG. 10 is a block diagram of another body worn device for monitoring physical activity and reporting calorie burn information, in accordance with at least one embodiment of the present invention.

Another embodiment of the body worn device is shown in FIG. 10. In the device of FIG. 10, the audio and radio functions have been removed. The display (12) is a multi-color indicator that signals daily activity progress status periodically or on demand with a user button (13) push. The percentage of progress is relative to the displayed color, where red equals very low progress, orange low progress, yellow is moderate progress, blue is good progress and green is goal achieved, where color transitions have personalized thresholds for each individual based upon their biometrics. The color indicator also delivers a blinking pattern when the battery (9) is being charged from the computer port (6). A single user button (13) allows for the on demand illumination of the color indicator or time marking various activity periods. In some embodiments, the real time clock (18), A/D converter, flash memory (4) and RAM (5) are incorporated within the CPU circuit (3). The device monitors and records user movements with a 3-axis acceleration sensor (1). These movements are processed by the device as acceleration units without converting them locally to calories. Daily goal and progress thresholds are evaluated by the device in terms of acceleration units (AU). Conversion of AU into calories is done externally by a web application. The thresholds for the color progress indicator and the ECP interval is configured within the device for specific individuals by the web application each time the device synchronizes with the application via the computer port(6). The progress thresholds are delivered to the device in terms of AUs.

The device monitors for extended sedentary periods of the user and alerts them when the ECP is near. Upon detection of a period of sedentary activity from the acceleration sensor, an interval timer is started. If the timer reaches the ECP prior to an exit from sedentary activity, an alert is delivered to the user.

At least one embodiment utilizes a vibration tactile warning, but audible and/or visual alerts can be used in other embodiments. The exit from sedentary activity is a two stage event. Any activity above the resting threshold suspends the timer. If the activity returns shortly to a sedentary level the timer resumes counting toward the ECP point from its previous position. If the activity persists for a duration and intensity above the ECP Reset threshold, the timer is reset.

Figure 11:
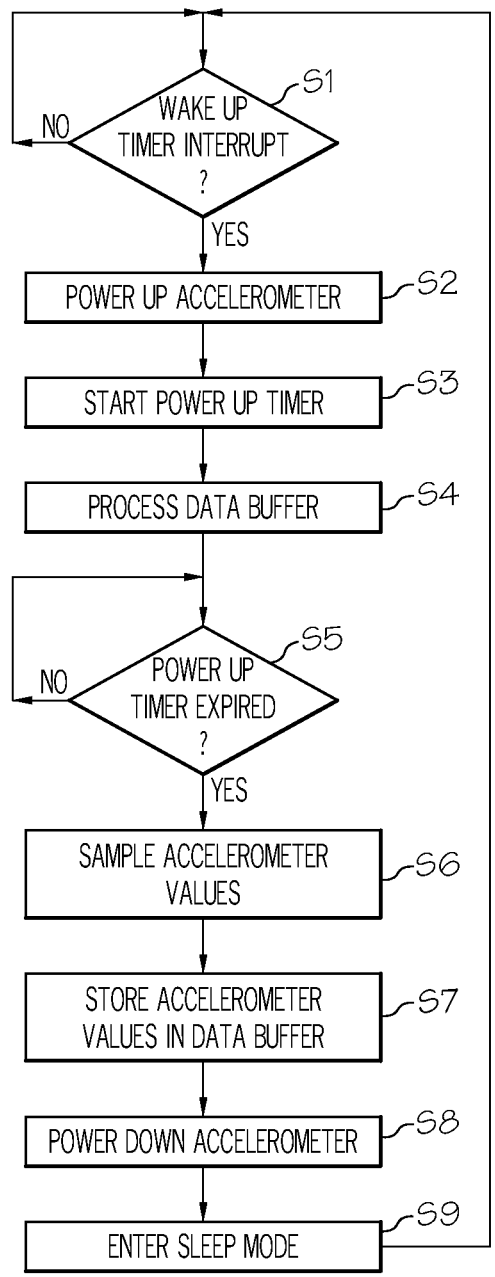
FIG. 11 is a flow diagram of a device sampling algorithm, in accordance with at least one embodiment of the present invention.

To minimize power consumption, the device is normally in a very low power standby mode, periodically waking, sampling the acceleration sensor, processing and storing the data and returning to standby. This mode of operation is illustrated by the flowchart of FIG. 11. As human body movements are characterized by the frequency range of approximately 0.5-3.5 Hz, a minimum sample frequency of the sensor is established as 10 Hz, being twice the Nyquist frequency plus guardband. The device sleeps until the 10 Hz interrupt occurs in S1. This timer interrupt is derived from the real time clock (18) of FIGS. 7-10 and is of sufficient accuracy to maintain sampling interval precision for the signal processing algorithms. Upon wakeup, the acceleration sensor (S2) is powered up. As there is a finite interval before a valid output is obtained, a power up timer is started (S3). To minimize wake time, a pipelined data processing method is employed, where the sampled data from the previous wake period is processed (S4) in parallel with the sensor power up interval. When the sensor outputs are known to be valid (S5), new data samples are acquired for all axes (S6) and stored in a data buffer (S7). This buffer is at least 10 samples deep to perform appropriate digital filtering. When the buffer is empty, 10 sample periods are required before the algorithms produce valid output. The sensor is powered down (S8) and the CPU re-enters a low power sleep mode (S9).

Figure 12:
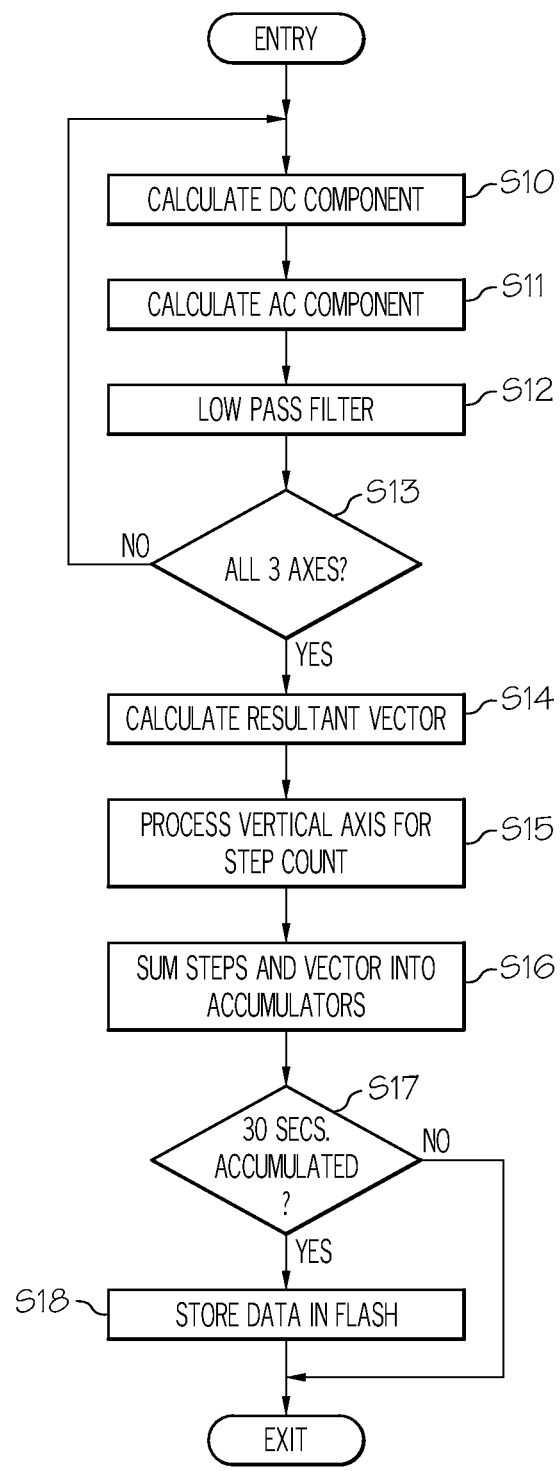
FIG. 12 is a flow diagram of a device signal processing algorithm, in accordance with at least one embodiment of the present invention.

The sampled data processing (S4) is expanded in flowchart FIG. 12. The steady state or DC component of the sensor signal is calculated (S10) by a 8 point moving average on the sample buffer. A running sum is maintained of the 8 point buffer. The oldest sample is subtracted from and the new sample added to the running sum. Division by 8 produces the moving average or DC component. At a 10 Hz sample frequency, this implements a FIR digital lowpass filter with a cutoff of approximately 0.55 Hz. The calculated DC component is subtracted from the original sensor signal to yield the AC component (S11). The AC component is low pass filtered (S12) at between about 3.5 Hz to less than about 5 Hz by implementing a 2 pole Chebyshev recursive IIR filter on the data buffer. The filtering is repeated for all axes (S13). The resultant acceleration vector is calculated as the square root of the sum of squares of the AC signals (S14): $A_v=(X_{AC}^2+Y_{AC}^2+Z_{AC}^2)^{0.5}$. The vertical Z axis is processed for step recognition (S15). The resultant vector and steps are summed into accumulator values (S16). Each 30 second interval (S17), the accumulated values are written to memory (S18), offering a 30 second time resolution for the activity record. The accumulator values are then cleared.

Figure 13:
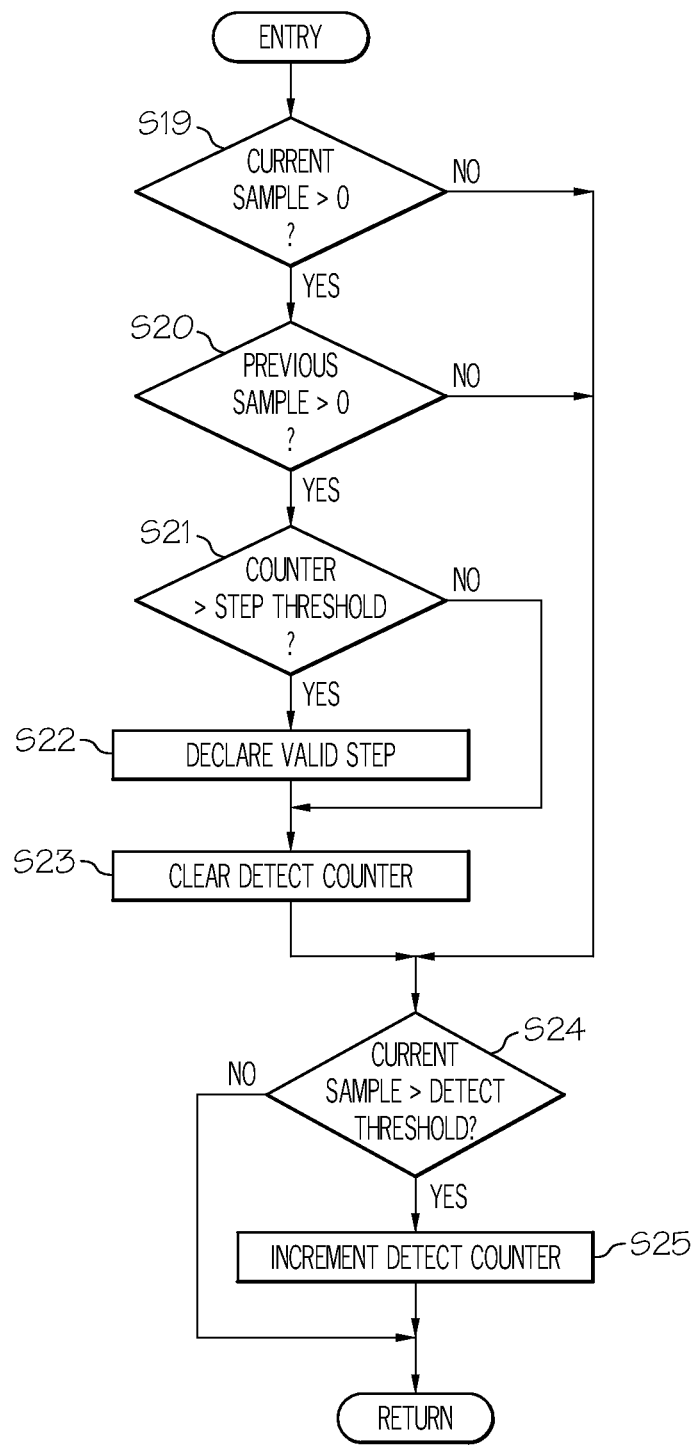
FIG. 13 is a flow diagram of a device step detection algorithm, in accordance with at least one embodiment of the present invention.
Figure 14:
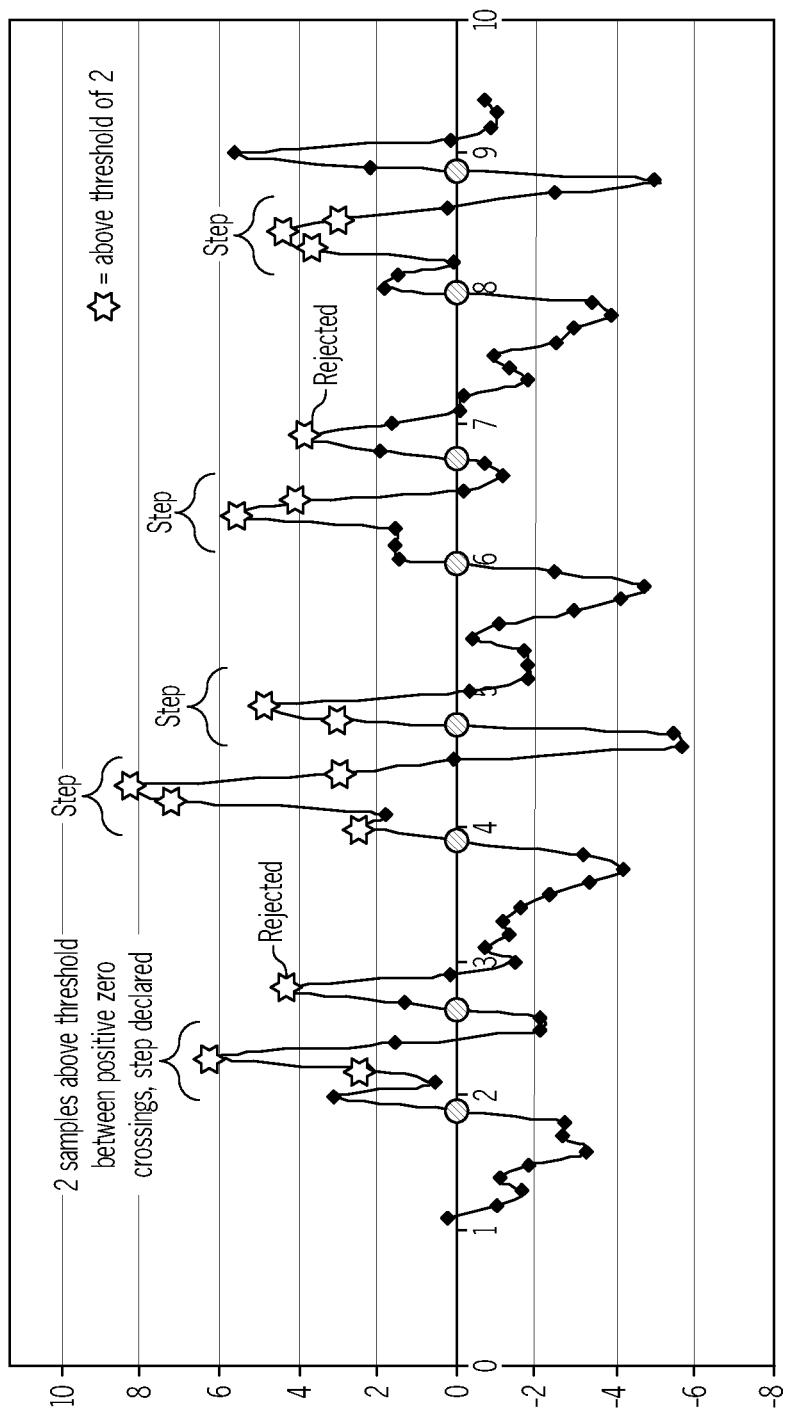
FIG. 14 is a vertical axis acceleration waveform, illustrating the classification of movements as steps, in accordance with at least one embodiment of the present invention.

The step recognition algorithm (S15) is expanded in flowchart FIG. 13. The algorithm monitors the AC component of the vertical Z axis for positive zero crossing. If the signal between zero crossings is of sufficient amplitude and duration as shown in FIG. 14, a step is declared. The algorithm operates at each new data sample to determine if a step is to be declared. A positive zero crossing detector is formed by decisions S19 and S20. If no positive zero crossing is present, the sample is tested against the amplitude threshold (S24); an example threshold of 2 is shown in FIG. 14. If the amplitude threshold is exceeded, a counter is incremented (S25). When a positive zero crossing is detected, the counter value is tested against an occurrence threshold (S21). If the number of samples above the amplitude threshold between successive positive zero crossings is greater than the occurrence threshold, a step is declared (S22). If the occurrence threshold is not met, the counter is reset (S23) and a new step detection sequence will commence.

FIG. 14 illustrates an example of an occurrence of an amplitude threshold of 2. The specific thresholds are dependent on the acceleration sensor sensitivity, noise floor and digital filter performance. The thresholds are experimentally optimized across a diverse population sample performing various walking and non-walking activities. By setting the thresholds to detect narrow, high amplitude signals, the algorithm is effective in detecting foot strikes and rejecting non-walking movements.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to". Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A device for predicting a resting metabolic rate of a person having a weight, height, age, and gender, the device comprising:

a controller having one or more inputs, the controller using resting diastolic and systolic blood pressure measurements as independent variables in a predictive equation, wherein the predictive equation is $$RMR = K_1 * W * (1 - K_2 * W/H^2) + K_3 * H - K_4 * A K_5 * G + K_6 * D - K_7 * S + K_8$$

wherein RMR is the resting metabolic rate of the person, W is the weight of the person, H is the height of the person, A is the age of the person, G is the gender of the person, D is the diastolic blood pressure of the person, S is the systolic blood pressure of the person, and $K_1$, $K_2$, $K_3$, $K_4$, $K_5$, $K_6$, $K_7$, and $K_8$ are constants.

* * * * *